US00PP34209P2

(12) United States Plant Patent
Bradford et al.

(10) Patent No.: US PP34,209 P2
(45) Date of Patent: May 10, 2022

(54) NECTARINE TREE NAMED 'CANDYSWEET XVI'

(50) Latin Name: *Prunus persica*
Varietal Denomination: Candysweet XVI

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,922

(22) Filed: Dec. 17, 2021

(51) Int. Cl.
*A01H 5/08* (2018.01)
*A01H 6/74* (2018.01)

(52) U.S. Cl.
USPC ..... Plt./190

(58) Field of Classification Search
USPC ..... Plt./187, 190
See application file for complete search history.

(56) References Cited

U.S. PATENT DOCUMENTS

PP14,249 P2 10/2003 Bradford
PP15,143 P2 9/2004 Bradford

*Primary Examiner* — Susan McCormick Ewoldt

(57) ABSTRACT

The present invention relates to a new and distinct variety of nectarine tree, *Prunus persica*, broadly characterized by a medium size, vigorous, hardy, self-fertile, productive and regular bearing tree. The variety has a large showy blossom and blooms during the mid season, with a chilling requirement of about 550 hours. The fruit matures under the ecological conditions described in mid to late Mid to late August, with first picking on Aug. 18, 2021. The fruit is uniform, large in size, sub-acidic and very sweet in flavor, mostly globose in shape, clingstone in type, firm in texture, yellow in flesh color, mostly red in skin color, and has a bitter tasting kernel.

1 Drawing Sheet

Botanical classification: *Prunus persica.*
Variety Denomination: 'CANDYSWEET XVI'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Candysweet XVI'.

The present variety was hybridized by us in 2005 as a first generation cross using 'Candy Pearl' (U.S. Plant Pat. No. 14,249) nectarine as the selected seed parent and 'August Bright' (U.S. Plant Pat. No. 15,143) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2010 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Candy Pearl' (U.S. Plant Pat. No. 14,249) nectarine by being vigorous, by being self-fertile, by having a large blossom, by having reniform leaf glands, and by producing nectarines that are mostly red in skin color, that are clingstone in type, and that are sub-acidic in flavor, but is quite distinguished from it by producing fruit that is yellow instead of white in flesh color, by being much sweeter in flavor, by having a bitter instead of sweet tasting kernel, and that ripen about forty-eight days later.

The present variety is most similar to its pollen parent, 'August Bright' (U.S. Plant Pat. No. 15,143) nectarine, by having a medium size tree, by being self-fertile, by having reniform leaf glands, and by producing nectarines that are mostly red in skin color, that are yellow in flesh color, that are clingstone in type, and that mature in mid August, but is distinguished therefrom by having a bitter instead of sweet kernel, by having a genetically large instead of small flower, and by producing fruit that is somewhat larger in size, sub-acidic instead of acidic in flavor, and much sweeter.

SUMMARY OF VARIETY

In summary, the present nectarine variety is characterized by a medium size, vigorous, hardy, self-fertile, productive and regular bearing tree. The variety has a large showy blossom and blooms during the mid season, with a chilling requirement of about 550 hours. The fruit matures under the ecological conditions described in mid to late Mid to late August, with first picking on Aug. 18, 2021. The fruit is uniform, large in size, sub-acidic and very sweet in flavor, mostly globose in shape, clingstone in type, firm in texture, yellow in flesh color, mostly red in skin color, and has a bitter tasting kernel.

DRAWING

The accompanying photograph consists of four whole fruits positioned to display the characteristics of the skin color and form, one divided fruit to reveal the flesh and stone, a tip shoot of new leaf growth, typical leaves, and three insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Aug. 23, 2021, on a multiplied tree on 'Nemaguard' (unpatented) rootstock during its tenth growing season. The blossom and flower descriptions were made the previous blooming season. All major color code designations are by reference to the Inter-Society Color Council, National Bureau of Standards. Common color names are also used occasionally.

PARENTAGE

Seed parent: 'Candy Pearl' (U.S. Plant Pat. No. 14,249) nectarine.

Pollen parent: 'August Bright' (U.S. Plant Pat. No. 15,143) nectarine.

TREE

Size: Medium, reaching and maintaining a height of 12' [3.66 m.] and a spread of 10' [3.05 m.] after ten growing seasons utilizing typical dormant pruning.

Vigor: Vigorous, responding about average to irrigation and fertilization. The variety grows about 2' [0.61 m.] of surplus top-growth during the spring and summer. The plant should be grown on a standard commercial rootstock for production purposes.

Growth: Upright and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 550 hours.

Leaf bud burst: Medium to late, toward the end of flowering.

Trunk:

*Size*.—Medium, reaching a maximum diameter of 5½" [140 mm.] after the tenth growing season.

*Texture*.—Medium to shaggy.

*Bark color*.—A Grayish yellowish brown [80. gy.yBr] and Grayish brown [61. gy.Br] variegation with Dark grayish brown [62. d.gy.Br] crevices present.

*Lenticels*.—Approximate Number Per Square Inch: 8. Color: Deep orange yellow [69. deep OY]. Average Size: ⅜" [9.5 mm.] in length. The width is typically one fourth as much as the length. Shape: Elongated.

Branches:

*Size*.—Medium, diameter of main scaffold is 2⅝" [66.7 mm.] measured 12" above the crotch, diameter of limb is 1⅝" [41.3 mm.] measured 12" above the first fork.

*Texture*.—Smooth to medium on first and second year wood, increasing in roughness with age.

*Color*.—1st Year Wood Topside: Grayish red [19. gy.R]. 1st Year Wood Underside: Brilliant yellow green [116. brill.YG]. Older Wood: A Moderate yellowish brown [77. m.yBr] and Deep yellowish brown [75. deep yBr] variegation with Dark yellowish brown [78. d.yBr] crevices present.

*Lenticels*.—Number Per Square Inch: About 35 on second year wood. Color: Strong yellowish brown [74. s.yBr]. Average Size: Small, 1/16" [1.6 mm.] in length. The width is typically one fourth as much as the length. Shape: Elongated.

Leaves:

*Size*.—Large. Average Length: 6" [152.4 mm.]. Average Width: 1⅞" [47.6 mm.].

*Arrangement*.—Alternate.

*Thickness*.—Medium.

*Form*.—Elliptical.

*Apex*.—Acuminate.

*Base*.—Rounded to acute with an average base angle of 75 degrees.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Petiole*.—Average Length: ½" [12.7 mm.]. Average Thickness: 1/16" [1.6 mm.]. Color: Moderate yellow green [120. m.YG].

*Stipules*.—Number: 2 per leaf, up to 6 per growing tip. Average Length: ¼" [6.4 mm.]. Color: Light greenish yellow [101. l.gY] becoming Moderate brown [58. m.Br] with age.

*Glands*.—Number: 2 to 4 per leaf. Position: Alternate, first pair is located at the intersection of petiole and base of blade. Form: Reniform. Size: Medium, about 1/32" [0.8 mm.] in length and 1/64" [0.4 mm.] in width. Color: Strong yellow green [117. s.YG].

*Leaf buds*.—Pointed.

Flower buds:

*Hardiness*.—Hardy, with respect to central California blooming season.

*Diameter*.—Typically ⅜" [9.5 mm.] 1 week before bloom.

*Length*.—Typically ⅝" [15.9 mm.] 1 week before bloom.

*Form*.—Not appressed.

*Surface*.—Pubescent.

*Tip color*.—Light purplish pink [249. l.pPk].

Flowers: Perfect, complete, perigynous, usually a single pistil, about thirty stamens, five sepal and petal locations alternately positioned.

*Type*.—Showy, large.

*Average flower diameter*.—1 13/16" [46.0 mm.].

*Average flower depth*.—½" [12.7 mm.] when fully open.

*Number of petals*.—Five, extra petal fragments rarely observed, double blossoms not observed.
*Petal arrangement*.—Overlapping.
*Petal shape*.—Circular to oval.
*Petal margin*.—Entire, very wavy.
*Average petal diameter*.—¾" [19.1 mm.].
*Average petal length*.—¾" [19.1 mm.].
*Petal apex*.—Rounded.
*Petal base*.—Rounded to slightly cordate.
*Petal color*.—Pale pink [7. p.Pk] toward the apex and Light pink [4. l.Pk] toward the base on both sides.
*Anthocyanin coloration intensity*.—Weak.
*Anther color*.—Light pink [4. l.Pk] surrounding a Light yellow [86. l.Y] center at bloom onset.
*Pollen*.—Anthers produce a moderate amount of Brilliant yellow [83. brill.Y] pollen.
*Stigma color*.—Light greenish yellow [101. l.gY].
*Stigma position*.—Typically located slightly above the nearby anthers.
*Stamen position*.—Typically located about 1/16" [1.6 mm] below the petals.
*Average pistil length*.—13/16" [20.6 mm.].
*Average stamen length*.—9/16" [14.3 mm.].
*Ovary*.—Non-pubescent.
*Sepal color*.—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—⅜" [9.5 mm.].
*Sepal width*.—5/16" [7.9 mm.].
*Sepal apex*.—Rounded to elliptical to match the sepal length and width.
*Sepal margin*.—Fairly smooth.
*Sepal outer surface*.—Pubescent.
*Fragrance*.—Moderate.
*Blooming period*.—Medium to late, blooms about three days after 'Majestic Pearl' (U.S. Plant Pat. No. 18,778) nectarine.
*Onset of bloom*.—One percent on Feb. 22, 2021.
*Date of full bloom*.—Mar. 5, 2021.
*Duration of bloom*.—One to two weeks, dependent on ambient temperature.
*Bloom density*.—Medium to heavy.
*Number per cluster*.—1 to 3 with single flowers most common.

FRUIT

Maturity when described: Firm ripe, Aug. 23, 2021.
Date of first picking: Aug. 18, 2021.
Date of last picking: Sep. 2, 2021.
Size: Uniform, large.
*Average diameter axially*.—3⅛" [79.4 mm.].
*Average diameter across suture plane*.—3⅛" [79.4 mm.].
*Average diameter across cheek plane*.—3 1/16" [77.8 mm.].
*Typical weight*.—10 ounces [283 grams].
Form: Fairly uniform, usually globose, most symmetrical, a few asymmetrical.
*Longitudinal section form*.—Most round, a few slightly oblong.
*Axial view*.—Round.
Suture: Extends from the stem cavity, along the sides, and ends about ½" [12.7 mm.] beyond the pistil point.
*Near the base*.—A sharp groove.
*Along the side*.—A shallow trough.
*Near the apex*.—A medium groove.
Ventral surface: Rounded, lipped throughout on both sides.
Lips: Equal along the sides, somewhat unequal at the apex.
Cavity: Flaring with Vivid orange yellow [66. v.OY] stem markings present.
*Depth*.—⅝" [15.9 mm.].
*Breadth*.—1¼" [31.8 mm.].
Base: Truncate.
Apex: Rounded, quite cordate if viewed parallel to the suture.
Pistil point: An inconspicuous Brilliant orange yellow [67. brill.OY] dot depressed within the suture of negligible length.
Stem: Medium.
*Average length*.—⅜" [9.5 mm.].
*Average width*.—3/16" [4.8 mm.].
Skin:
*Thickness*.—Medium.
*Surface*.—Smooth.
*Tenacity*.—Tenacious to the flesh.
*Astringency*.—Non-astringent.
*Tendency to crack*.—None observed.
*Color*.—Dark red [16. d.R] over a Deep reddish orange [36. deep rO] background with some Brilliant yellow [83. brill.Y] areas where sun protected and with Strong orange yellow [68. s.OY] freckling mostly toward the apex.
Flesh:
*Color*.—Brilliant orange yellow [67. brill.OY] with Vivid deep purplish red [257. v.deep pR] bleeding toward the stone.
*Surface of pit cavity*.—Covered with Vivid deep purplish red [257. v.deep pR] broken fibers when twisted away from the stone.
*Amygdalin*.—Scarce.
*Juice*.—Moderate.
*Texture*.—Firm, crisp.
*Fibers*.—Abundant, fine, tender.
*Ripens*.—Fairly even, slightly earlier toward the apex.
*Flavor*.—Sub-acidic, very sweet, typically 22 brix.
*Aroma*.—Very slight.
*Eating quality*.—Excellent.

STONE

Type: Clingstone.
Form: Oval.
Hilum: Narrow, oval.
Base: Rounded.
Apex: Rounded to obtuse.
Sides: Equal.
Tip: Negligible.
Surface: Irregularly furrowed toward the apex, pitted toward the base.
Ridges: Jagged.
External color: Strong reddish brown [40. s.rBr] when first removed.
Pit wall color when cracked: Moderate yellowish brown [77. m.yBr].
Cavity surface color: Deep yellowish brown [75. deep yBr].
Average pit wall thickness: ¼" [6.4 mm.].
Average length: 1 7/16" [36.5 mm.].
Average width: 1 1/16" [27.0 mm.].
Average breadth: 15/16" [23.8 mm.].
Tendency to split: None observed.

Kernel:

*Form*.—Oval.

*Skin color*.—Moderate orange yellow [71. m.OY].

*Pellicle color*.—Dark grayish yellowish brown [81. d.gy.yBr].

*Vein color*.—Dark orange yellow [72. d.OY].

*Taste*.—Bitter.

*Viable*.—Yes.

*Average length*.—13/16" [20.6 mm.].

*Average width*.—9/16" [14.3 mm.].

*Amygdalin*.—Abundant.

USE

Market: Fresh market and long distance shipping.

Keeping quality: Good, fruit quality observed to remain in good condition after 17 days in standard cold room at 36° Fahrenheit [2° Celsius].

Shipping quality: Good.

Resistance to insects: Not tested.

Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'August Bright' (U.S. Plant Pat. No. 15,143) nectarine, by having a medium size tree, by being self-fertile, by having reniform leaf glands, and by producing nectarines that are mostly red in skin color, that are yellow in flesh color, that are clingstone in type, and that mature in mid August, but is distinguished therefrom by having a bitter instead of sweet kernel, by having a genetically large instead of small flower, and by producing fruit that is somewhat larger in size, sub-acidic instead of acidic in flavor, and much sweeter.

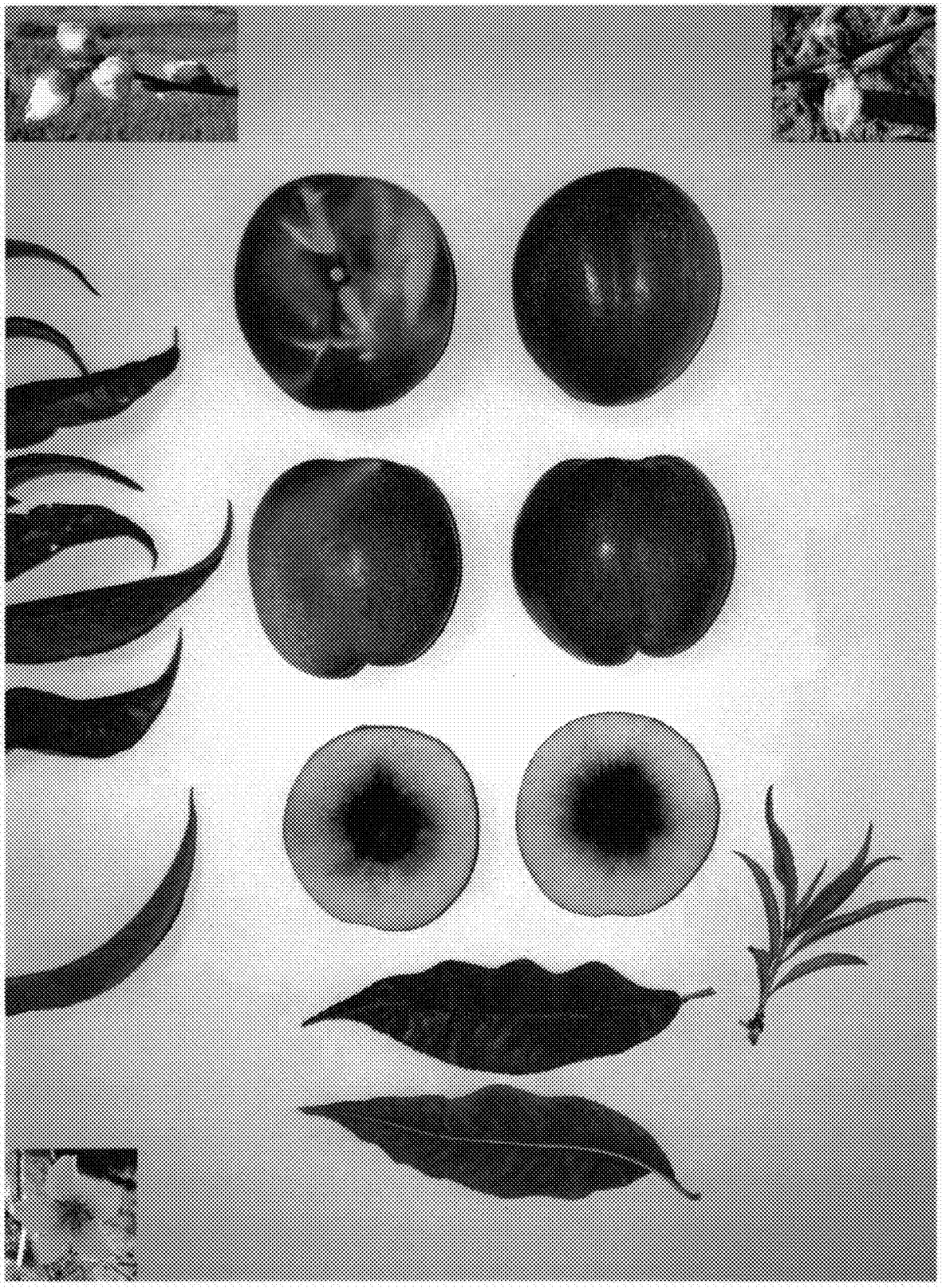

* * * * *